United States Patent [19]

Marrelli et al.

[11] Patent Number: 5,576,974
[45] Date of Patent: Nov. 19, 1996

[54] METHOD AND APPARATUS FOR DETERMINING WATERCUT FRACTION AND GAS FRACTION IN THREE PHASE MIXTURES OF OIL, WATER AND GAS

[75] Inventors: John D. Marrelli, Houston; Farhan Siddiqui, Katy, both of Tex.

[73] Assignee: Texaco Inc., White Plains, N.Y.

[21] Appl. No.: 228,614

[22] Filed: Apr. 15, 1994

[51] Int. Cl.$^6$ .................................... G01N 22/00
[52] U.S. Cl. .................... 364/554; 364/509; 364/510; 73/861.04; 324/640; 324/637
[58] Field of Search ..................... 324/640, 643, 324/637, 639; 73/861.38, 861.04; 364/509, 510, 554; 372/122, 123

[56] References Cited

U.S. PATENT DOCUMENTS

| | | | |
|---|---|---|---|
| 4,499,418 | 2/1985 | Helms et al. | 324/637 |
| 4,947,127 | 8/1990 | Helms et al. | 324/640 |
| 4,947,377 | 12/1990 | Durrett et al. | 324/640 |
| 5,014,434 | 3/1991 | Marrelli | 324/640 |
| 5,048,340 | 9/1991 | Thompson et al. | 73/597 |
| 5,107,219 | 4/1992 | Marrelli et al. | 324/640 |
| 5,127,272 | 7/1992 | Dean et al. | 73/861.04 |
| 5,195,380 | 3/1993 | Hatton et al. | 73/861.04 |
| 5,386,719 | 2/1995 | Marrelli et al. | 364/640 DR |

OTHER PUBLICATIONS

Lin et al; "The measurement of Crude Oil/Natural Gas/WaterFlow Rates by Using Microwave Technique", SPE, pp. 387–391 Sep. 1990.

*Primary Examiner*—Emanuel T. Voeltz
*Assistant Examiner*—Kamini S. Shah
*Attorney, Agent, or Firm*—Kenneth R. Priem; James L. Bailey; Richard A. Morgan

[57] ABSTRACT

The gas fraction of a multiphase fluid is determined using 'on-line' statistical methods and then using that fraction to compute the correct water fraction. The gas fraction ($X_g$) is detected by using the standard deviation of the raw phase (Pstd), maximum phase in the sampling interval (Pmax), average phase (Pavg) or standard deviation of attenuation (Astd) data and maximum attenuation in the sampling interval (Amax), or average attenuation (Aavg) from streams flowing in the water fraction monitor sensor cell where the conditions are determined.

5 Claims, No Drawings

METHOD AND APPARATUS FOR DETERMINING WATERCUT FRACTION AND GAS FRACTION IN THREE PHASE MIXTURES OF OIL, WATER AND GAS

BACKGROUND OF THE INVENTION

1. The Field of the Invention

The present invention concerns on-line statistical analysis of microwave determination of the gas fraction in three phase mixtures of oil, water and gas.

2. The Prior Art

There presently are no instruments making only two measurements and using statistical methods capable of predicting the ratios of oil, water and gas in a multiphase stream. The TEXACO STARCUT® monitor described in U.S. Pat. Nos. 4,499,418 and 4,947,127, the disclosures of which are incorporated herein by reference, is enhanced by the present invention to allow prediction of the ratios of oil, water and gas. There are many applications where a three-phase water cut monitor which does not require separation of the fluid phases will save millions of dollars in construction costs by obviating the requirement for a three-phase separation facility. Furthermore, experience shows that gas (and therefore errors in instruments not insensitive to gas) is present to some extent in virtually all live crude oil handling operations. For example, in primary well head production situations, even if no gas is expected initially, gas will surely result due to pipeline pressure drops and with aging of the reservoir. The choice of a low gas water cut monitor can save the cost of constructing three phase and even two phase separation facilities.

Field experience has shown that all known instruments designed to determine water fraction are sensitive to the presence of gas in the flowing mixture. The presence of gas tends to reduce the reading of water fraction, even though the actual water fraction has not changed. Experience has also shown that gas is usually present in live crude handling pipelines. It has therefore been a high priority to develop methods of reducing the effects of gas on water cut monitors.

SUMMARY OF THE INVENTION

The subject microwave water fraction monitor is a new field application for the continuous measurement of the percent water in crude oil production streams over the entire 0% to 100% range. It is a continuous recording water fraction monitor functioning from 0% to 100% water fraction regardless of temperature, salinity, crude oil API gravity and the presence of gas. The monitor can continuously report emulsion status (water-continuous or oil-continuous), salinity, density of the hydrocarbon phase and estimate gas fraction. Operator interaction is minimized by features such as automatic self-calibration, unattended operation at remote locations, remote access options through SCADA systems and self-starting after power outages. Safe operation in oil field locations is assured and instrument performance has been demonstrated over a wide variety of conditions including slug flow, free gas and salinity and crude density changes.

An object of the present invention is to provide a water fraction monitor which has accurate measurement of water/oil ratios despite changes in oil composition, gas fraction, emulsion state, water salinity, temperature changes and flow rate changes. The same basic model has been put into operation on the downstream side of test separators as well as directly on wellhead production streams.

DETAILED DESCRIPTION OF THE PRESENT INVENTION

The present invention, in general, consists of determining the gas fraction in the fluid using 'on-line' statistical methods, detailed below, and then using that fraction to compute the correct water fraction. The subject three-phase water fraction monitor includes the following:

1. Gas fraction (Xg) is detected by using the standard deviation of the raw phase (Pstd), maximum phase in the sampling interval (Pmax), average phase (Pavg) or standard deviation of attenuation (Astd) data and maximum attenuation in the sampling interval (Amax), or average attenuation (Aavg) from streams flowing in the water fraction monitor sensor cell where, for the condition stated:

Gas Fraction

Case 1: $Xg = K1 * Pstd$;

Case 2: $Xg = K2 * Astd$;

Case 3: $Xg = K3 * Pstd / Pavg$, normalized by the amount of water;

Case 4: $Xg = K4 * Astd / Aavg$, normalized by the amount of water and not sensitive to errors in wavelength;

Case 5: $Xg = K5 * Pstd / Pmax$, normalized by maximum water fraction in data set;.

Case 6: $Xg = K6 * Astd / Amax$, normalized by maximum water fraction in data set but not sensitive to errors in wavelength;

Case 7: $Xg = K5 * (Pmax - Pavg) / Pmax$, a form of standard derivation, but useful when data sets are small;

Case 8: $Xg = K6 * (Amax - Aavg) / Amax$, a form of standard derivation, but useful when data sets are small and not sensitive to wavelength errors;

Case 9: $Xg = [K7 * K8 * EXP(Pavg/K9)] * Pstd$, improved fit for the curve of Case 5;

Case 10: $Xg = [K10 * K11 * EXP(Aavg/K12)] * Astd$, improved fit for the curve of Case 6;

Case 11: $Xg = f\{Astd, Pstd, Amax, Pmax, Aavg, Pmax\}$, general relationship recognizing that $X_g$ is a function of all parameters.

All of the above cases have validity under some or all of the operating conditions in the above mentioned STARCUT® monitor. Software detects appropriate conditions and selects the gas fraction equation for those conditions. See case selection below.

2. Water fraction measurement (the ratio of water volume to total liquid measure) has been made insensitive to gas fraction using the following equation:

$$\text{WATER FRACTION} = X_w / \{1 - X_g\}$$

where $X_w$ = Water Fraction

A water fraction monitor incorporating the above measures will be substantially insensitive to the gas fraction of a three phase fluid mixture.

Discussion of CASES of equation validity:

a. Small gas fractions less than 5%
   CASES 1 & 2 b. Gas fraction calculations are weighted by water fraction
   CASES 3, 4, 5, 6, 7, 8, 9, 10, 11 c. Pure Liquid properties are inferred from Maximum data in sampling interval
   CASES 5, 6, 7, 8 d. Low water fraction
   CASES 1, 2, 9, 10, 11
e. High water fraction
   CASES 1, 2, 3, 4, 5, 6, 7, 8, 9, 10, 11
f. If there is a possibility of making errors in, i.e. the number of wavelengths passing through the sample, logical phase shifter circle selection, phase dependent methods of gas detection should not be used. Use:
   CASES 2, 4, 6, 8, 10, 11
g. High Gas Fraction
   CASES 9, 10, 11

The accuracy of the subject instrument is greatly enhanced if the fluids are well mixed and the relative velocity of the individual components are approximately the same. A sidestream version of a known water cut monitor, such as the one described in U.S. Pat. No. 5,001,434, the disclosure of which is incorporated herein by reference, is recommended for use in low gas situations, (defined as less than 50% gas by volume at the pressure of the measurement or whenever the liquid is the continuous phase).

When the gas fraction is greater that 50%, or whenever the gas is in the continuous phase, then "Incline" type piping, such as that described in U.S. Pat. Nos. 5,048,348; 5,127,272; and 5,195,380, the disclosures of which are incorporated herein by reference, is recommended.

Field testing has revealed three types of flow conditions which are not easily detectable by the operators.

1. Free gas is generally present in all production facilities, including the liquid leg of two-phase separators.
2. Water fraction may change back and forth from 0% to 100% oil or water several times in a few minutes due to separation of oil and water in the pipeline as it flows from the well head. This slugging effect is often present, to some degree, in offshore wells.
3. Leaking manifold valves cause well tests to be inaccurate due to co-mingled flow from other wells. Co-mingled flow can be identified by a change in water salinity, as detected by the subject monitor. Because free gas, slugging and co-mingling of fluids could reduce the accuracy of metering equipment, considerable effort has been applied to studies of the effects of microwave transmission on mixtures of gas, oil and salt water and the detection of rapidly changing events. The subject monitor's auto-calibration capability, detection speed (>300 samples/second) and immunity to the effects of free gas and salinity changes has been enhanced by electronic improvements, computer upgrade and improved algorithms incorporating increased knowledge of gas/liquid dielectric properties. As a consequence of these improvements, mixtures of fluids containing gas content variations from 0% to 25%, salinity changes from fresh water to 50,000 parts/million of salts, and rapid slugging between oil and water, may be monitored without significant reduction in the accuracy of water fraction readings. Salinity and API gravity estimates for the water and oil components improve with time and may be continuously read from current loop outputs or from computer generated graphics resident in the control room.

The wide variety of oil reservoirs and production conditions precludes selection of a "standard set" of expectable properties as design parameters. An effective water fraction instrument should have the capability to automatically adapt to a wide range of conditions. The subject meter was developed to provide this automatic adaptation to changing conditions as well as to improve on the accuracy of traditional methods of water fraction determination. When long pipelines show slugging behavior, that is, rapid and large swings in water fraction, crude oil and brine production can vary between oil-continuous and water-continuous emulsions, in some cases as often as once per minute. Instrument calibrations dependent on the assumption that the fluids are always oil continuous, such as capacitance meters, therefore have a high probability of error in such cases. Other types of water cut instruments, which depend on knowing the density of the production component fluids, are extremely sensitive to the presence of free gas. Field conditions such as variable temperature, salinity, and crude oil gravity or density also contribute significantly to error in traditional methods of water cut measurement. The design of the subject meter assumed that measurement of oil-water ratio in production systems requires determining as many of the parameters of the production fluids as is necessary to accurately specify the water fraction. These parameters are water salinity, crude oil gravity, temperature and free gas fraction. A frequency of approximately 10,000 mega Hertz was chosen as the frequency likely to provide the most information about the fluids through which it is transmitted. The technology underlying the development of this meter may be separated into three general areas:

1) Electronic Design;
2) Fluid Property Analysis; and
3) Automatic Calibration.

A sampling system has been developed which ensures that a representative sample is continuously provided to the monitor regardless of conditions of the flow. These sampling systems are described elsewhere.

The sensor element is machined from a solid bar of inconel steel, acts as a precision tolerance, high pressure, microwave waveguide which channels and shapes the transmitted microwave energy as it passes through the crude oil stream. The sensor cell is mounted to the side of an explosion proof enclosure which contains all of the electronics, including a miniature 386 microcomputer. The sensor cell includes an oil and temperature resistant dielectric material embedded in the steel to fill part of the waveguide and determine the calibration properties of the sensor. The sensor is also connected to a pipeline sidestream sampling system by way of a 3-way valve. The 3-way valve provides opportunity to verify system accuracy by allowing the trapping of fluids for analysis as they pass through the sensor. The objective of the electronic system is to accurately deliver a microwave signal to the sensor waveguides and measure the change in properties of the microwave signal after it has been transmitted through the live oil stream. This signal is then compared to a similarly treated signal passed through a reference fluid held in a cell in the same inconel block and at the same temperature of the crude by its proximity to the flow lines. The electronic detection is achieved with methods of differential recording which minimize error due to noise or internal drift. Simultaneous electrical measurement of two effects of dielectric properties of the production, attenuation and phase shift, allow considerable enhancement of the monitor's ability to detect and compensate for the effects of rapidly varying gas bubble flow. Further compensation of electronic drift is provided by computer-based calibration curves for those electronic components which have shown special sensitivity to operation temperature of the electronics. In some field installations, the electronic enclosure may experience a 40° F. temperature change during one day. The monitor operation is controlled by a miniature, industrially hardened microcomputer packaged with the sensor in a single compact unit installed at the pipeline site.

Microwave transmission through space is governed by the complex dielectric permitivity of the medium. The properties of the three mixture components, oil, water and gas, their proportions and way in which they are mixed determine the mixture dielectric. The complex dielectric of the medium controls both the attenuation of the transmitted signal and the velocity of transmission. In the monitor these two phenomena are measured in terms of: 1) the power transmitted through the sensor cell, referred to here as attenuation in decibels; and 2) the change in phase shift of the received sinusoidally oscillating wave relative to a stable fluid reference, referred to here as phase shift measured in degrees. Both measurements are made relative to similar measurements of a highly stable calibration fluid sealed within the inconel sensor block. Values of attenuation and phase shift are also dependent on the sensor geometry. While it is possible to convert the relative attenuation and relative phase shift to the complete dielectric, a measure independent of sensor geometry, that information has not been presented here as it is not directly related to the detection of water fraction. Study of the chemical properties of fluids is divided into properties of non-polar liquids (oils) alone, polar liquids (brine) alone, gases and mixtures of polar, non-polar fluids and gases.

All functions of the subject water fraction monitor depend on microwave attenuation and phase shift data, some stored in computer memory and some automatically collected during operation in the field. The standard method used for water fraction monitor prediction depends on laboratory data stored in the monitor's memory. The present invention assumes that no matter how much gas is in the production fluid, some gas-free liquid samples will pass through the sensor. As low gas samples eventually pass the sensor, the monitors estimation of the correct density and salinity will converge to minimum values which will be correct and also provide the best estimate of the liquid curves from which water fraction is determined. In several minutes, thousands of data points are accumulated and evaluated searching for the best estimates of the production curves. At operator selected intervals, depending on well test schedules and which can vary from hours to days, accumulated data is discarded and new search for the correct curves is initiated to allow new wells with different properties to be automatically evaluated.

The gas-free analysis depends on the observation in laboratory and field that regardless of gas fraction some of the production flowing pass the sensor will contain gas-free samples. Furthermore, since the all-liquid lines are defined now on the cross-plot, estimates of gas fraction are made by the distance of data points from the liquid lines. This estimate is less precise with greater deviation from the liquid line. A portion of current research is directed toward accurately determining gas fraction from deviation from the liquid lines. Once the cross-plot curves are generated, decision criteria are set up by creating a line connecting the 100% water and 100% oil cross-plot points, to determine if subsequent data is from oil or water-continuous fluids. Finally, using the decision curve, the proper water fraction versus phase calibration curve is chosen and water fraction is read.

The subject microwave water fraction monitor is designed for installation at a wellhead to continuously monitor the production stream. It can also be configured for installation on wet oil transport pipelines, to monitor the percent water in the liquid line from two phase separators or carryover water in the oil line of three phase separators. Offshore, test separators and test lines are a substantial cost element of new developments. The microwave system can reduce well and production test facilities continuous reading device also costs in many applications. The enhances opportunities to optimize reservoir management and obtain improved facilities performance. The system is sufficiently compact to be mounted at wellhead locations and within existing production and/or test facilities with minor modifications to the existing piping. It is capable of accurately measuring the water fraction of an oil-continuous emulsion, a water-continuous emulsion or a water and oil mixture over a 0% to 100% water fraction range even though properties of the fluids are changing and up to 25% gas may be present. The unit can also provide estimates of water phase salinity and crude oil density. Qualitative estimates of free gas present in the sample stream are available. Its low power consumption and rugged construction makes it applicable for use in remote locations. The system functions as a stand alone water fraction meter or as a diagnostic device for the performance of separator facilities. The system has been packaged for sub-sea metering applications and its continuous output can be transmitted by existing communications networks such as SCADA systems.

The present invention may be subject to many modifications and changes without departing from the spirit or essential characteristics thereof. The present embodiment should therefor be considered in all respects as being illustrative and not restrictive of the scope of the invention as defined by the appended claims.

We claim:

1. In conjunction with a fluid fraction of oil and water measuring means, a method to determine water fraction comprising the steps of:

performing a statistically significant number of measurements of phase shift and attenuation of a microwave signal passing through or reflected from a petroleum stream;

determining statistical measures on each of these data such as the means, the average, the standard deviation, the kurtosis, the maximum value and the minimum value;

forming a separate table of values of each of the data which correlate each statistical measure on each datum with an estimate of gas fraction in the petroleum stream;

forming a separate table of values of each of these data which correlate algebraic combinations of statistical measures on each datum with an estimate of gas fraction in the petroleum stream;

determining, as a function of the average water fraction and the average estimate of gas fraction, by using the equation:

$$Water\ Fraction = Xw/(1-Xg)$$

where Xw is the previous estimate of water fraction and Xg is the gas fraction, an improved value of water fraction estimate; and providing a means for reporting said improved value of water fraction estimate on a record medium.

2. The method according to claim 1 in which the new estimate of water fraction is used to recompute the estimate of gas fraction and in this way converge on a yet more accurate estimate of gas fraction when gas fraction estimate is dependent on a water fraction estimate.

3. The method according to claim 2 wherein the improved gas estimate is used to gain an improved water fraction estimate.

4. The method according to claim 3 in which alternately estimating gas fraction and the water fraction continues until the estimates of gas and water fractions no longer change by a preset amount.

5. In conjunction with a fluid fraction of oil and water measuring means, a method to determine gas fraction comprising the steps of:

making a statistically significant number of measurements of phase shift and attenuation of a microwave signal passing through or reflecting from a petroleum stream;

determining statistical measures on these data such as the means, the average, the standard deviation, the kurtosis, the maximum value, and the minimum value of each datum;

determining a constant multiplier Vi between the statistical estimate of at least one measured property of the petroleum stream and the true gas fraction measured by an independent method including using published data in which gas fraction of the petroleum stream being measured is correlated with the pressure at which the petroleum stream content is held in a sealed container using standard industry methods;

forming the ratio Ki of the true gas fraction to the statistical estimate value Vi;

using Ki on a multiplier of the statistical estimate Vi to generate an improved estimate of the gas fraction; and creating a separate table of values which correlate each statistical estimate with a gas fraction in the petroleum stream as an output.

* * * * *